US008013212B2

(12) United States Patent
O'Gorman et al.

(10) Patent No.: US 8,013,212 B2
(45) **Date of Patent: *Sep. 6, 2011**

(54) SITE-SPECIFIC RECOMBINATION IN EUKARYOTES AND CONSTRUCTS USEFUL THEREFOR

(75) Inventors: Stephen O'Gorman, San Diego, CA (US); Geoffrey Wahl, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/494,203

(22) Filed: Jun. 29, 2009

(65) Prior Publication Data

US 2009/0286320 A1 Nov. 19, 2009

Related U.S. Application Data

(62) Division of application No. 11/437,556, filed on May 19, 2006, now Pat. No. 7,566,814, which is a division of application No. 08/919,501, filed on Aug. 28, 1997, now Pat. No. 7,135,608.

(51) Int. Cl.

| | |
|---|---|
| ***C12N 15/82*** | (2006.01) |
| ***C12N 15/87*** | (2006.01) |
| ***C12N 15/00*** | (2006.01) |
| ***C07H 21/04*** | (2006.01) |
| ***A01H 5/00*** | (2006.01) |

(52) U.S. Cl. ..... 800/287; 800/278; 800/298; 435/320.1; 536/24.1

(58) Field of Classification Search ........................ None
See application file for complete search history.

(56) References Cited

U.S. PATENT DOCUMENTS

| | | | | |
|---|---|---|---|---|
| 4,870,009 | A | 9/1989 | Evans et al. | 435/70 |
| 4,952,496 | A | 8/1990 | Studier et al. | 435/91 |
| 5,477,002 | A * | 12/1995 | Tuttle et al. | 800/303 |
| 5,654,182 | A | 8/1997 | Wahl et al. | 435/172.1 |
| 5,925,808 | A | 7/1999 | Oliver et al. | 800/298 |
| 6,096,545 | A * | 8/2000 | Lefebvre et al. | 435/410 |
| 6,723,896 | B1 * | 4/2004 | Moller et al. | 800/288 |
| 7,135,608 | B1 * | 11/2006 | O'Gorman et al. | 800/8 |
| 7,566,814 | B2 * | 7/2009 | O'Gorman et al. | 800/287 |

FOREIGN PATENT DOCUMENTS

WO WO 92/15694 9/1992

OTHER PUBLICATIONS

Rommens et al. 1992, Mol. Gen. Genet. 231:433-441.*
Twell et al. 1991, Genes. Dev. 5:496-507.*
Maeser et al Mol. Gene. Genet. 230:170-176.*
Kilby et al 1995, The Plant Journal 8:637-652.*
Dzelzkalns et al. 1993, The Plant Cell 5:855-863.*
Aladjem, et al., "Positive Selection of FLP-Mediated Unequal Sister Chromatid Exchange Products in Mammalian Cells" *Molecular and Cellular Biology* 17 (2):857-861 (1997).
Dale and Ow, "Gene transfer with subsequent removal of the selection gene from the host genome" *Proc. Natl. Acad. Sci. USA* 88:10558-10562 (1991).
O'Gorman, et al., "Protamine-Cre recombinase transgenes efficiently recombine target sequences in the male germ line of mice, but not in embryonic stem cells" *Proc. Natl. Acad. Sci. USA* 94:14602-14607 (1997).
Orban, et al., "Tissue- and site-specific DNA recombination in transgenic mice" *Proc. Natl. Acad. Sci. USA* 89:6861-6865 (1992).
Qin, et al., "Cre recombinase-mediated site-specific recombination between plant chromosomes" *Proc. Natl. Acad Sci. USA* 91:1706-1710 (1994).
Zambrowicz and Palmiter, "Testis-Specific and Ubiquitous Proteins Bind to Functionally Important Regions of the Mouse Protamine-1 Promoter" *Biology of Reproduction* 50:65-72 (1994).
Twell et al. 2001. Genes. Dev. 5:496-507.
Lakso et al., Efficient in vivo manipulation of mouse genomic sequences at the zygote stage. Proc. Nat. Acad. Sci. USA, 93: 5860-5865, Jun. 1996.
Wall et al., Transgenic dairy cattle: Genetic engineering on a large scale. J. Dairy Science, 80:2213-2224, 1997.
Mullins and Mullins, Perspectives Series: Molecular medicine in genetically engineered animals. J. Clin. Invest., 98 (11): Supplement 1996, S37-S40.
Robi and Heideman, Production of transgenic rats and rabbits. In *Transgenic Animal Technology, A Laboratory Handbook*. Chapter 9, p. 265-270, 1994.

(Continued)

*Primary Examiner* — Li Zheng
(74) *Attorney, Agent, or Firm* — Foley & Lardner LLP; Stephen E. Reiter

(57) ABSTRACT

Site-specific recombinases provide a means of efficiently manipulating chromosomal sequences in mammalian cells in culture and in mice. Embryonic stem cells containing recombinase nucleic acid constructs that were expressed in the male germline would simplify current protocols for producing mice bearing homologously recombined alleles that have been secondarily rearranged by a site-specific recombinase, five lines of transgenic mice containing a fusion gene consisting of the mouse protamine 1 gene promoter and the Cre recombinase coding sequence (ProCre nucleic acid constructs) showed high levels of Cre-mediated recombination of the germline, but did not show appreciable recombination in other tissues. In different ProCre strains, between 80% and 100% of the progeny that inherited a Cre target nucleic acid construct from males that were also heterozygous for a ProCre nucleic acid construct inherited the Cre-recombined target. ProCre nucleic acid constructs and recombined targets segregated in the first generation. When ES cells prepared from one ProCre line were transfected with vectors containing a loxP-flanked neomycin cassette, G418 resistant, homologously recombined clones, in which the loxP sites remained functional, were readily isolated. These data establish that ProCre nucleic acid constructs will facilitate the production of subtle, conditional, or tissue-specific mutations in mice as well as the production and analysis of mice with recombinase-conditional lethal alleles.

9 Claims, 2 Drawing Sheets

OTHER PUBLICATIONS

Ahearn et al., "Cloning and Sequence Analysis of the Mouse Genomic Locus Encoding the Largest Subunit of RNA PolymeraseII" *The Journal of Biological Chemistry* 262 (22):10695-10705 (1987).
Albanesi et al., "A cell- and developmental stage-specific promotor drives the expression of a truncated c-*kit* protein during mouse spermatid elongation" *Development* 122:1291-1302 (1996).
Araki et al., "Site-specific Recombinase, R, Encoded by Yeast Plasmid pSR1" *J Mol. Biol.* 225:25-37 (1992).
Araki et al., "Site-specific recombination of a transgene in fertilized eggs by transient expression of Cre recombinase" *Proc. Natl. Acad. Sci. USA* 92:160-164 (1995).
Askew et al., "Site-Directed Point Mutations in Embryonic Stem Cells: a Gene-Targeting Tag-and-Exchange Strategy" *Molecular and Cellular Biology* 13 (7):4115-4124 (1993).
Beddington et al., "An in situ transgenic enzyme marker for the midgestation mouse embryo and the visualization of inner cell mass clones during early organogenesis" *Development* 106:37-46 (1989).
Behringer et al., "Heart and bone tumors in transgenic mice" *Proc. Natl. Acad Sci. USA* 85:2648-2652 (1988).
Braun et al., "Genetically haploid spermatids are phenotypically diploid" *Nature* 337:373-376 (1989).
Broach and Hicks, "Replication and Recombination Functions Associated with the Yeast Plasmid, 2μ Circle" *Cell* 21:501-508 (1980).
Brusa et al., "Early-Onset Epilepsy and Postnatal Lethality Associated with an Editing-Deficient *GluR-B* Allele in Mice" *Science* 270:1677-1680 (1995).
Caldwell and Handel, "Protamine transcript sharing among postmeiotic spermatids" *Proc. Natl. Acad. Sci USA* 88:2407-2411 (1991).
Dzelzkalns et al., "Distinct *cis*-Acting Elements Direct Pistil-Specific and Pollen-Specific Activity of the *Brassica* S Locus Glycoprotein Gene Promotor" *The Plant Cell* 5:855-863 (1993).
Evan et al., "Isolation of Monoclonal Antibodies Specific for Human c-*myc* Proto-Oncogene Product" *Molecular and Cellular Biology* 5 (12):3610-3616 (1985).
Eyal et al., "Pollen Specificity Elements Reside in 30 bp of the Proximal Promotors of Two Pollen-Expressed Genes" *The Plant Cell* 7:373-384 (1995).
Feil et al., "Ligand-activated site-specific recombination in mice" *Proc. Natl. Acad. Sci USA* 93:10887-10890 (1996).
Fiering et al., "An in-out" strategy using gene targeting and FLP recombinase for the functional dissection of complex DNA regulatory elements: Analysis of the β-globin locus control region *Proc. Natl. Acad. Sci. USA* 90:8469-8473 (1993).
Fiering et al., "Targeted deletion of 5'HS2 of the murine β-globin LCR reveals that it is not essential for proper regulation of the β-globin locus" *Genes & Development* 9:2203-2213 (1995).
Gu et al., "Deletion of a DNA Polymerase β Gene Segment in T Cells Using Cell Type-Specific Gene Targeting" *Science* 265:103-106 (1994).
Gu et al., "Independent Control of Immunoglobulin Switch Recombination at Individual Switch Regions Evidenced through Cre-*loxP*-Mediated Gene Targeting" *Cell* 73:1155-1164(1993).
Hasty et al., "Introduction of a subtle mutation into the *Hox-2.6* locus in embryonic stem cells" *Nature* 350:243-246 (1991).
Hecht et al., "Evidence fo Haploid Expression of Mouse Testicular Genes" *Experimental Cell Research* 164:183-190 (1986).
Hoess et al., "P1 site-specific recombination: Nucleotide sequence of the recombining sites" *Proc. Natl. Acad. Sci. USA* 79:3398-3401 (1982).
Howard et al., "Sperm-Specific Expression of Angiotensin-Converting Enzyme (ACE) is Mediated by a 91-Base-Pair Promoter Containing a CRE-Like Element" *Molecular and Cellular Biology* 13 (1):18-27 (1993).
Howard et al., "The VirD2 Protein of *A. tumefaciens* Contains a C-Terminal Bipartite Nuclear Localization Signal: Implications for Nuclear Uptake of DNA in Plant Cells" *Cell* 68:109-118 (1992).
Jefferson et al., "GUS fusions: β-glucuronidase as a sensitive and versatile gene fusion marker in higher plants" *The EMBO Journal* 6 (13):3901-3907 (1987).
Kalderon et al., "A Short Amino Acid Sequence Able to Specify Nuclear Location" *Cell* 39:499-509 (1984).
King et al., "Deletion Mapping by Immunoselection against the H-Y Histocompatibility Antigen Further Resolves the $Sxr^{\alpha}$ Region of the Mouse Y Chromosome and Reveals Complexity of the *Hya* Locus" Genomics 24:159-168 (1994).
Kitamoto et al., "Humanized Prion Protein Knock-in by Cre-Induced Site-Specific Recombination in the Mouse" *Biochemical and Biophysical Research Communications* 222 (3):742-747 (1996).
Klein et al., "High-velocity microprojectiles for delivering nucleic acids into living cells" *Nature* 327:70-73 (1987).
Kozak, Marilyn, "Point Mutations Define a Sequence Flanking the AUG Initiator Codon That Modulates Translation by Eukaryotic Ribosomes" *Cell* 44:283-292 (1986).
Kühn et al., "Inducible Gene Targeting in Mice" *Science* 269:1427-1429 (1995).
Lakso et al., "Targeted oncogene activation by site-specific recombination in transgenic mice" *Proc. Natl. Acad. Sci. USA* 89:6232-6236 (1992).
Lewandoski et al., "*Zp3*-cre, a transgenic mouse line for the activation or inactivation of *loxP*-flanked target genes specifically in the female germ line" *Curr Biol* 7:148-151 (1997).
Logie et al., "Ligand-regulated site-specific recombination" *Proc Natl Acad Sci* 92:5940-5944 (1995).
Mansour et al., "Disruption of the proto-oncogene *int-2* in mouse embryo-derived stem cells: a general strategy for targeting mutations to non-selectable genes" *Nature* 336:348-352 (1988).
McCormick (1991b) Transformation of tomato with *Agrobacterium tumefaciens*, in Plant Tissue Culture Manual, K. Linsey, Ed B6:1-9.
Nakamura and inouye, "DNA Sequence of the Gene for the Outer Membrane Lipoprotein of *E. coli*: an Extremely AT-Rich Promoter" *Cell* 18:1109-1117 (1979).
No et al., "Ecdysone-inducible gene expression in mammalian cells and transgenic mice" *Proc. Natl. Acad Sci USA* 93:3346-3351 (1996).
O'Gorman et al., "Recombinase-Mediated Gene Activation and Site-Specific Integration in Mammalian Cells" *Reports* 251:1351-1355 (1991).
Olson et al., "Know Your Neighbors: three Phenotypes in Null Mutants of the Myogenic bHLH Gene *MRF4" Cell* 85:1-4 (1996).
Onouchi et al., "Visualization of site-specific recombination catalyzed by a recombinase from *Zygosaccharomyces rouxii* in *Arabidopsis thaliana" Mol Gen Genet* 247:653-660 (1995).
Ow et al., "Transient and Stable Expression of the Firefly Luciferase Gene in Plant Cells and Transgenic Plants" *Science* 234:856-859 (1986).
Peschon et al., "Expression of Mouse Protamine 1 Genes in Transgenic Mice" *Ann N Y Acad Sci* 564:186-197 (1989).
Peschon et al., "Spermatid-specific expression of protamine 1 in transgenic mice" *Proc. Natl. Acad. Sci. USA* 84:5316-5319 (1987).
Robertson (1987) Teratocarcinomas and embryonic stem cells, a practical approach, eds. E. J. Robertson (IRL Press), pp. 71-112.
Robertson et al., "Germ-line transmission of genese introduced into cultured pluripotential cells by retroviral vector" *Nature* 323:445-448 (1986).
Schickler et al., "A Mouse Oocyte-Specific Protein That Binds to a Region of mZP3 Promotor Responsible for Oocyte-Specific mZP3 Gene Expression" *Molecular and Cellular Biology* 12 (1):120-127 (1992).
Schwenk et al., "A *cre*-transgenic mouse strain for the ubiquitous deletion of *IoxP*-flanked gene segments including deletion in germ cells" *Nucleic Acids Research* 23 (24):5080-5081 (1995).
Simpson et al., "Genetics variation among 129 substrains and its importance for targeted mutagenesis in mice" *Nature Genetics* 16:19-27 (1997).
Soriano and Jaenisch, "Retroviruses as Probes for Mammalian Development: Allocation of Cells to the Somatic and Germ Cell Lineages" *Cell* 46:19-29 (1986).
Studier et al., "Use of T7 RNA Polymerase to Direct Expression of Cloned Genes" *Methods in Enzymology* 185:60-89 (1990).
Thomas and Capecchi, "Site-Directed Mutagenesis by Gene Targeting in Mouse Embryo-Derived Stem Cells" *Cell* 51:503-512 (1987).

Twell et al., "Pollen-Specific gene expression in transgenic plants: coordinate regulation of two different tomate gene promoters during micropsporogenesis" *Development* 109:705-713 (1990).
Twell et al., "Promotor analysis of genes that are coordinately expressed during pollen development reveals pollen-specific enhancer sequences and shared regulatory elements" *Genes & Development* 5:496-507 (1991).
Twell et al., "Transient Expression of Chimeric Genes Delivered into Pollen by Microprojectile Bombardments[1]" *Plant Physiol.* 91:1270-1274 (1989).
Tybulewicz et al., "Neonatal Lethality and Lymphopenia in Mice with a Homozygous Disruption of the c-*abl* Proto-Oncogene" *Cell* 65:1153-1163 (1991).
Weterings et al., "Functional dissection of the promoter of the pollen-specific gene *NTP303* reveals a novel pollen-specific, and conserved *cis*-regulatory element" *The Plant Journal* 8 (1):55-63 (1995).
Zambrowicz et al., "Analysis of the mouse protamine 1 promoter in transgenic mice" *Proc. Natl. Acad. Sci. USA* 90:5071-5075 (1993).
Zhou et al., "Identification of Tow Positive Transcriptional Elements Within the 91-Base Pair Promoter for Mouse Testis Angiotensin Converting Enzyme (Testis ACE)" *Development Genetics* 16:201-209 (1995).
International Search Report dated Nov. 10, 1998 in related application PCT/US98/17852.
Notice of Allowance dated Mar. 16, 2006 in related U.S. Appl. No. 08/919,501.
US Notice of Allowance dated Apr. 6, 2009 in related U.S. Appl. No. 11/437,566.
US Notice of Allowance dated Jun. 8, 2009 in related U.S. Appl. No. 11/437,556.
US Office Action dated Dec. 11, 2007 in related U.S. Appl. No. 11/437,556.
US Office Action dated Jul. 9, 2008 in related U.S. Appl. No. 11/437,556.

* cited by examiner

SEQUENCE LISTING

```
<160> NUMBER OF SEQ ID NOS: 8

<210> SEQ ID NO 1
<211> LENGTH: 652
<212> TYPE: DNA
<213> ORGANISM: Mus musculus

<400> SEQUENCE: 1

gtctagtaat gtccaacacc tccctcagtc caaacactgc tctgcatcca tgtggctccc      60

atttatacct gaagcacttg atggggcctc aatgttttac tagagcccac ccccctgcaa     120

ctctgagacc ctctggattt gtctgtcagt gcctcactgg ggcgttggat aatttcttaa     180

aaggtcaagt tccctcagca gcattctctg agcagtctga agatgtgtgc tttcacagtt     240

acaaatccat gtggctgttt cacccacctg cctggccttg ggttatctat caggacctag     300

cctagaagca ggtgtgtggc acttaacacc taagctgagt gactaactga acactcaagt     360

ggatgccatc tttgtcactt cttgactgtg acacaagcaa ctcctgatgc caaagccctg     420

cccacccctc tcatgcccat atttggacat ggtacaggtc ctcactggcc atggtctgtg     480

aggtcctggt cctctttgac ttcataattc ctaggggcca ctagtatcta taagaggaag     540

agggtgctgg ctcccaggcc acagcccaca aaattccacc tgctcacagg ttggctggct     600

cgacccaggt ggtgtcccct gctctgagcc agctcccggc caagccagca cc             652


<210> SEQ ID NO 2
<211> LENGTH: 29
<212> TYPE: DNA
<213> ORGANISM: Artificial Sequence
```

<220> FEATURE:
<223> OTHER INFORMATION: Description of Artificial Sequence: Synthetic
primer

<400> SEQUENCE: 2
gtctagtaat gtccaacacc tccctcagt 29

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
primer

<400> SEQUENCE: 3
ctctgagcca gctcccggcc aagccagcac c 31

<210> SEQ ID NO 4
<211> LENGTH: 1022
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 4
atggagcaaa agctgatttc tgaggaggat ctgggaggac ccaagaagaa gaggaaggtg 60
tccaatttac tgaccgtaca ccaaaatttg cctgcattac cggtcgatgc aacgagtgat 120
gaggttcgca agaacctgat ggacatgttc agggatcgcc aggcgttttc tgagcatacc 180
tggaaaatgc ttctgtccgt ttgccggtcg tgggcggcat ggtgcaagtg aataaccgga 240
aatggtttcc cgcagaacct gaagatgttc gcgattatct tctatatctt caggcgcgcg 300
gtctggcagt aaaaactatc cagcaacatt tgggccagct aaacatgctt catcgtcggt 360
ccgggctgcc acgaccaagt gacagcaatg ctgtttcact ggttatgcgg cggatccgaa 420
aagaaaacgt tgatgccggt gaacgtgcaa aacaggctct agcgttcgaa cgcactgatt 480
tcgaccaggt tcgttcactc atggaaaata gcgatcgctg ccaggatata cgtaatctgg 540
catttctggg gattgcttat aacaccctgt tacgtatagc cgaaattgcc aggatcaggg 600
ttaaagatat ctcacgtact gacggtggga gaatgttaat ccatattggc agaacgaaaa 660
cgctggttag caccgcaggt gtagagaagg cacttagcct gggggtaact aaactggtcg 720
agcgatggat ttccgtctct ggtgtagctg atgatccgaa taactacctg ttttgccggg 780
tcagaaaaaa tggtgttgcc gcgccatctg ccaccagcca gctatcaact cgcgccctgg 840
aagggatttt tgaagcaact catcgattga tttacggcgc taaggatgac tctggtcaga 900
gatacctggc ctggtctgga cacagtgccc gtgtcggagc cgcgcgagat atggcccgcg 960
ctggagtttc aataccggag atcatgcaag ctggtggctg gaccaatgta aatattgtca 1020
tg 1022

<210> SEQ ID NO 5
<211> LENGTH: 2293
<212> TYPE: DNA
<213> ORGANISM: Artificial Sequence
<220> FEATURE:
<223> OTHER INFORMATION: Description of Artificial Sequence: Synthetic
nucleotide sequence

<400> SEQUENCE: 5
gtctagtaat gtccaacacc tccctcagtc caaacactgc tctgcatcca tgtggctccc 60

```
atttatacct gaagcacttg atggggcctc aatgttttac tagagcccac ccccctgcaa    120
ctctgagacc ctctggattt gtctgtcagt gcctcactgg ggcgttggat aatttcttaa    180
aaggtcaagt tccctcagca gcattctctg agcagtctga agatgtgtgc tttcacagtt    240
acaaatccat gtggctgttt cacccacctg cctggccttg ggttatctat caggacctag    300
cctagaagca ggtgtgtggc acttaacacc taagctgagt gactaactga acactcaagt    360
ggatgccatc tttgtcactt cttgactgtg acacaagcaa ctcctgatgc caaagccctg    420
cccacccctc tcatgcccat atttggacat ggtacaggtc ctcactggcc atggtctgtg    480
aggtcctggt cctctttgac ttcataattc ctaggggcca ctagtatcta taagaggaag    540
agggtgctgg ctcccaggcc acagcccaca aaattccacc tgctcacagg ttggctggct    600
cgacccaggt ggtgtcccct gctctgagcc agctcccggc caagccagca cccgggacca    660
tggagcaaaa gctgatttct gaggaggatc tgggaggacc caagaagaag aggaaggtgt    720
ccaatttact gaccgtacac caaaatttgc ctgcattacc ggtcgatgca acgagtgatg    780
aggttcgcaa gaacctgatg gacatgttca gggatcgcca ggcgttttct gagcatacct    840
ggaaaatgct tctgtccgtt tgccggtcgt gggcggcatg gtgcaagttg aataaccgga    900
aatggtttcc cgcagaacct gaagatgttc gcgattatct tctatatctt caggcgcgcg    960
gtctggcagt aaaaactatc cagcaacatt tgggccagct aaacatgctt catcgtcggt   1020
ccgggctgcc acgaccaagt gacagcaatg ctgtttcact ggttatgcgg cggatccgaa   1080
aagaaaacgt tgatgccggt gaacgtgcaa aacaggctct agcgttcgaa cgcactgatt   1140
tcgaccaggt tcgttcactc atggaaaata gcgatcgctg ccaggatata cgtaatctgg   1200
catttctggg gattgcttat aacaccctgt tacgtatagc cgaaattgcc aggatcaggg   1260
ttaaagatat ctcacgtact gacggtggga gaatgttaat ccatattggc agaacgaaaa   1320
cgctggttag caccgcaggt gtagagaagg cacttagcct gggggtaact aaactggtcg   1380
agcgatggat ttccgtctct ggtgtagctg atgatccgaa taactacctg ttttgccggg   1440
tcagaaaaaa tggtgttgcc gcgccatctg ccaccagcca gctatcaact cgcgccctgg   1500
aagggatttt tgaagcaact catcgattga tttacggcgc taaggatgac tctggtcaga   1560
gatacctggc ctggtctgga cacagtgccc gtgtcggagc cgcgcgagat atggcccgcg   1620
ctggagtttc aataccggag atcatgcaag ctggtggctg gaccaatgta aatattgtca   1680
tgaactatat ccgtaacctg gatagtgaaa caggggcaat ggtgcgcctg ctggaagatg   1740
gcgattagcc attaacgcgt aaatgattgc tataattatt tgatatttat ggtgacatat   1800
gagaaaggat ttcaacatcg acggaaaata tgtagtgctg tctgtaagca ctaatattca   1860
gtcgccagcc gacattgtca ctgtaaagct gagcgataga atgcctgata ttgactcaat   1920
atccggtgcg tttcctgtca aaagtatgcg tagtgctgaa catttcgcga tgaatcccac   1980
cgaggaagaa gcacggcgcg gttttgctaa agtgatgtct gagtttggcg aactcttggg   2040
taaggttgga attgtcgagg ctgggtgtgg cggaccgcta tcaggacata gcgttggcta   2100
cccgtgatat tgctgaagag cttggcggcg aatgggctga ccgcttcctc gtgctttacg   2160
gtatcgccgc tcccgattcg cagcgcatcg ccttctatcg ccttcttgac gagttcttct   2220
gaggggatcg gcaataaaaa gacagaataa aacgcacggg tgttgggtcg tttgttcgga   2280
tcgatccgtc gac                                                      2293
```

<210> SEQ ID NO 6
<211> LENGTH: 86

```
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 6

cccgggatca attcaccatg ggaataactt cgtatagcat acattatacg aagttatgga     60

tccgccgcta tcaggacata gcgttg                                          86


<210> SEQ ID NO 7
<211> LENGTH: 4172
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 7

gcacttttcg gggaaatgtg cgcggaaccc ctatttgttt atttttctaa atacattcaa     60

atatgtatcc gctcatgaga caataaccct gataaatgct tcaataatat tgaaaaagga    120

agagtatgag tattcaacat ttccgtgtcg cccttattcc cttttttgcg gcattttgcc    180

ttcctgtttt tgctcaccca gaaacgctgg tgaaagtaaa agatgctgaa gatcagttgg    240

gtgcacgagt gggttacatc gaactggatc tcaacagcgg taagatcctt gagagttttc    300

gccccgaaga acgttttcca atgatgagca cttttaaagt tctgctatgt ggcgcggtat    360

tatcccgtat tgacgccggg caagagcaac tcggtcgccg catacactat tctcagaatg    420

acttggttga gtactcacca gtcacagaaa agcatcttac ggatggcatg acagtaagag    480

aattatgcag tgctgccata accatgagtg ataacactgc ggccaactta cttctgacaa    540

cgatcggagg accgaaggag ctaaccgctt ttttgcacaa catgggggat catgtaactc    600

gccttgatcg ttgggaaccg gagctgaatg aagccatacc aaacgacgag cgtgacacca    660

cgatgcctgt agcaatggca acaacgttgc gcaaactatt aactggcgaa ctacttactc    720

tagcttcccg gcaacaatta atagactgga tggaggcgga taaagttgca ggaccacttc    780

tgcgctcggc ccttccggct ggctggttta ttgctgataa atctggagcc ggtgagcgtg    840

ggtctcgcgg tatcattgca gcactggggc cagatggtaa gccctcccgt atcgtagtta    900

tctacacgac ggggagtcag gcaactatgg atgaacgaaa tagacagatc gctgagatag    960

gtgcctcact gattaagcat tggtaactgt cagaccaagt ttactcatat atactttaga   1020

ttgatttaaa acttcatttt taatttaaaa ggatctaggt gaagatcctt tttgataatc   1080

tcatgaccaa aatcccttaa cgtgagtttt cgttccactg agcgtcagac cccgtagaaa   1140

agatcaaagg atcttcttga gatccttttt ttctgcgcgt aatctgctgc ttgcaaacaa   1200

aaaaaccacc gctaccagcg gtggtttgtt tgccggatca agagctacca actctttttc   1260

cgaaggtaac tggcttcagc agagcgcaga taccaaatac tgtccttcta gtgtagccgt   1320

agttaggcca ccacttcaag aactctgtag caccgcctac atacctcgct ctgctaatcc   1380

tgttaccagt ggctgctgcc agtggcgata agtcgtgtct taccgggttg gactcaagac   1440

gatagttacc ggataaggcg cagcggtcgg gctgaacggg gggttcgtgc acacagccca   1500

gcttggagcg aacgacctac accgaactga gatacctaca gcgtgagcta tgagaaagcg   1560

ccacgcttcc cgaagggaga aaggcggaca ggtatccggt aagcggcagg gtcggaacag   1620

gagagcgcac gagggagctt ccagggggaa acgcctggta tctttatagt cctgtcgggt   1680

ttcgccacct ctgacttgag cgtcgatttt tgtgatgctc gtcagggggg cggagcctat   1740
```

```
ggaaaaacgc cagcaacgcg gcctttttac ggttcctggc cttttgctgg ccttttgctc   1800
acatgttctt tcctgcgtta tcccctgatt ctgtggataa ccgtattacc gcctttgagt   1860
gagctgatac cgctcgccgc agccgaacga ccgagcgcag cgagtcagtg agcgaggaag   1920
cggaagagcg cccaatacgc aaaccgcctc tccccgcgcg ttggccgatt cattaatgca   1980
gctggcacga caggtttccc gactggaaag cgggcagtga gcgcaacgca attaatgtga   2040
gttagctcac tcattaggca ccccaggctt tacactttat gcttccggct cgtatgttgt   2100
gtggaattgt gagcggataa caatttcaca caggaaacag ctatgaccat gattacgcca   2160
agctcgaaat taaccctcac taaagggaac aaaagctggg tacgaattca gatctcccgg   2220
gatcaattca ccatgggaat aacttcgtat agcatacatt atacgaagtt atggatccgg   2280
tcgagcagtg tggttttgca agaggaagca aaaagcctct ccacccaggc ctggaatgtt   2340
tccacccaat gtcgagcagt gtggttttgc aagaggaagc aaaaagcctc tccacccagg   2400
cctggaatgt ttccacccaa tgtcgagcaa accccgccca gcgtcttgtc attggcgaat   2460
tcgaacacgc agatgcagtc ggggcggcgc ggtcccaggt ccacttcgca tattaaggtg   2520
acgcgtgtgg cctcgaacac cgagcgaccc tgcagccaat atgggatcgg ccattgaacs   2580
agatggattg cacgcaggtt ctccggccgc ttgggtggag aggctattcg gctatgactg   2640
ggcacaacag acaatcggct gctctgatgc cgccgtgttc cggctgtcag cgcaggggcg   2700
cccggttctt tttgtcaaga ccgacctgtc cggtgccctg aatgaactgc aggacgaggc   2760
agcgcggcta tcgtggctgg ccacgacggg cgttccttgc gcagctgtgc tcgacgttgt   2820
cactgaagcg ggaagggact ggctgctatt gggcgaagtg ccggggcagg atctcctgtc   2880
atctcacctt gctcctgccg agaaagtatc catcatggct gatgcaatgc ggcggctgca   2940
tacgcttgat ccggctacct gcccattcga ccaccaagcg aaacatcgca tcgagcgagc   3000
acgtactcgg atggaagccg gtcttgtcga tcaggatgat ctggacgaag agcatcaggg   3060
gctcgcgcca gccgaactgt tcgccaggct caaggcgcgc atgcccgacg gcgaggatct   3120
cgtcgtgacc catggcgatg cctgcttgcc gaatatcatg gtggaaaatg gccgcttttc   3180
tggattcatc gactgtggcc ggctgggtgt ggcggaccgc tatcaggaca tagcgttggc   3240
tacccgtgat attgctgaag agcttggcgg cgaatgggct gaccgcttcc tcgtgcttta   3300
cggtatcgcc gctcccgatt cgcagcgcat cgccttctat cgccttcttg acgagttctt   3360
ctgaggggat cggcaataaa aagacagaat aaaacgcacg ggtgttgggt cgtttgttcg   3420
gatagggatc aattcaccat gggaataact tcgtatagca tacattatac gaagttatgg   3480
atccactagt tctagagcgg ccgccaccgc ggtggagctc caattcgccc tatagtgagt   3540
cgtattacaa ttcactggcc gtcgttttac aacgtcgtga ctgggaaaac cctggcgtta   3600
cccaacttaa tcgccttgca gcacatcccc ctttcgccag ctggcgtaat agcgaagagg   3660
cccgcaccga tcgcccttcc caacagttgc gcagcctgaa tggcgaatgg gacgcgccct   3720
gtagcggcgc attaagcgcg gcgggtgtgg tggttacgcg cagcgtgacc gctacacttg   3780
ccagcgccct agcgcccgct cctttcgctt tcttcccttc ctttctcgcc acgttcgccg   3840
gctttccccg tcaagctcta aatcgggggc tccctttagg gttccgattt agtgctttac   3900
ggcacctcga ccccaaaaaa cttgattagg gtgatggttc acgtagtggg ccatcgccct   3960
gatagacggt ttttcgccct ttgacgttgg agtccacgtt ctttaatagt ggactcttgt   4020
tccaaactgg aacaacactc aaccctatct cggtctattc ttttgattta taagggattt   4080
tgccgatttc ggcctattgg ttaaaaaatg agctgattta acaaaaattt aacgcgaatt   4140
```

-continued

```
ttaacaaaat attaacgctt acaatttagg tg                                    4172


<210> SEQ ID NO 8
<211> LENGTH: 34
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 8

ataacttcgt atagcataca ttatacgaag ttat                                    34
```

SITE-SPECIFIC RECOMBINATION IN EUKARYOTES AND CONSTRUCTS USEFUL THEREFOR

RELATED APPLICATIONS

This application is a division of U.S. patent application Ser. No. 11/437,556, filed May 19, 2006, now U.S. Pat. No. 7,566, 814, which is a division of U.S. patent application Ser. No. 08/919,501, filed Aug. 28, 1997, now U.S. Pat. No. 7,135, 608, the entire contents of each of which are hereby incorporated by reference herein for all purposes.

FIELD OF THE INVENTION

The present invention relates to methods for manipulating chromosomal sequences in cells by site-specific recombination promoted by recombinases. In a particular aspect, the present invention relates to methods for producing embryonic stem cells bearing nucleic acid sequences that have been rearranged by a site-specific recombinase expressed from a construct controlled by a tissue-specific promoter (e.g., a germline specific promoter). In another aspect, the present invention relates to methods for producing embryonic stem cells bearing nucleic acid sequences that have been rearranged by a site-specific recombinase expressed from a construct controlled by a conditional promoter.

BACKGROUND OF THE INVENTION

The analysis of gene function has increasingly come to require the production of subtle, tissue-specific, and conditional mutations in animals and plants. Although there are a number of methods for engineering subtle mutations in embryonic stem (ES) cells (Hasty et al. (1991) *Nature* 350: 243-246, Askew et al. (1993) *Mol Cell Bio*) 13:4115-4124), the use of site-specific recombinases to remove the selectable marker that permits isolation of homologously recombined ES cell clones has become increasingly prevalent (Kitamoto et al. (1996) *Biochem Diophys Res Commun* 222:742-747, Fiering et al. (1993) *Proc Natl Acad Sci USA* 90:8469-8473, Schwenk et al. (1995) *Nucleic Acids Res* 23:5080-5081; Gu et al. (1993) *Cell* 13:1155-1164; Sailer et al. (1996) *Taniguchi Symposia on Brain Sciences*, eds. Hakanishi et al. (Japan Scientific Press), pp. 89-98).

Site-specific recombinases represent the best method for creating tissue-specific and conditional mutations in animals and plants being employed first to remove the selectable marker to create a functionally wild-type allele, and then to inactivate the allele mosaically in animals and plants by removing some essential component in a tissue-specific or conditional manner (Ciu et al. (1994) Science 265:103-106; Kuhn et al. (1995) *Science* 269:1427-1429). Current protocols for using excessive site-specific recombination to remove selectable markers include transiently transfecting ES cell clones with a recombinase expression vector (Gu et al., (1993) Cell 73:1155-1164), microinjecting fertilized oocytes containing the recombinant allele with a recombinase expression vector (Kitamoto et al. (1996) *Biochem Biophys Res Commun* 222:742-747; Araki et al. (1995) *Proc Natl Acad Sci USA* 92:160-164), or breeding animals and plants containing the recombinant allele to animals and plants, respectively, containing a recombinase transgene (Schwenk et al. (1995) *Nucleic Acids Res* 23:5080-5081; Lewandoski et al. (1997) *Curr Biol* 7:148-151). Each of these approaches requires an investment of some combination of time, resources, and expertise over that required to generate animals and plants with homologously recombined alleles. The most commonly employed method, the secondary transfection of homologously recombined ES cell clones with a recombinase expression vector, additionally requires extended culture time that may decrease their potential to enter the germline.

In principle, marker excision would be substantially simplified through the use of ES cells containing recombinase nucleic acid constructs that were expressed in the germline, but not to an appreciable extent in the ES cells themselves or somatic tissues of animals and plants. The lack of ES cell expression would mean that targeting vectors containing selectable markers flanked by recombinase target sites could be used to isolate homologous recombinants without fear that the marker would be excised during culture. Robust recombinase expression in gametes would mean that the marker would be excised in at least some of the progeny of ES cell chimeras. Only a single step would be required to isolate subtle mutations and, if two different recombinase systems were employed, conditional and tissue-specific alleles could be produced with similar improvements in efficiency. A germline-specific recombinase nucleic acid construct could also be used to deliver recombined target nucleic acid constructs to the early embryo (Lewandoski et al. (11997) *Curr Biol* 7:148-151), so long as the recombined target was not detrimental to the terminal stages of spermatogenesis.

Previous reports have shown that expression of nucleic acid constructs containing the proximal promoter of the mouse protamine 1 (mP1) locus is restricted to haploid spermatids in mature mice (Peschon et al. (1987) *Proc Natl Acad Sci USA* 84:5316-5319; Behringer et al. (1988) *Proc Natl Acad Sci USA* 85: 2648-2652) although low levels of ectopic expression may occur in some mature tissues (Behringer et al. (1988) *Proc Natl Acad Sci USA* 85:2648-2652). Inclusion of the mP1 promoter does not guarantee expression in the male germline, however, for although nucleic acid constructs containing the mP1 promoter and the SV40 T-antigen coding sequence were transcribed, the message was not translated at detectable levels in spermatids (Behringer et al. (1988) *Proc Natl Acad Sci USA* 85: 2648-2652).

Accordingly, there is a need in the art for methods to modulate expression of recombined target nucleic acid sequences in the early embryo. In addition, there is a need in the art for tissue-specific and conditional recombinatory tools to create transgenic animals and plants. These and other needs in the art are addressed by the present invention.

BRIEF DESCRIPTION OF THE INVENTION

The present invention meets the need in the art for modulating expression of recombined target nucleic acid sequences to the early embryo. The present invention further meets the need in the art for tissue-specific and conditional recombinatory tools to create transgenic animals and plants. Thus, in accordance with the present invention, it has been discovered that nucleic acid constructs encoding a germline specific promoter operatively associated with a recombinase coding sequence lead to efficient recombination of a target nucleic acid construct in the male germline, but not in other tissues. This suggests that such nucleic acid constructs could be used for the efficient production of embryos bearing conditional, genetically lethal alleles. It has additionally been discovered that ES cell lines generated from one of these transgenic lines could be used in combination with targeting vectors that contained loxP-flanked selectable markers to isolate homologous recombinants containing the marker and functional loxP sites.

DETAILED DESCRIPTION OF THE INVENTION

Figure 1:
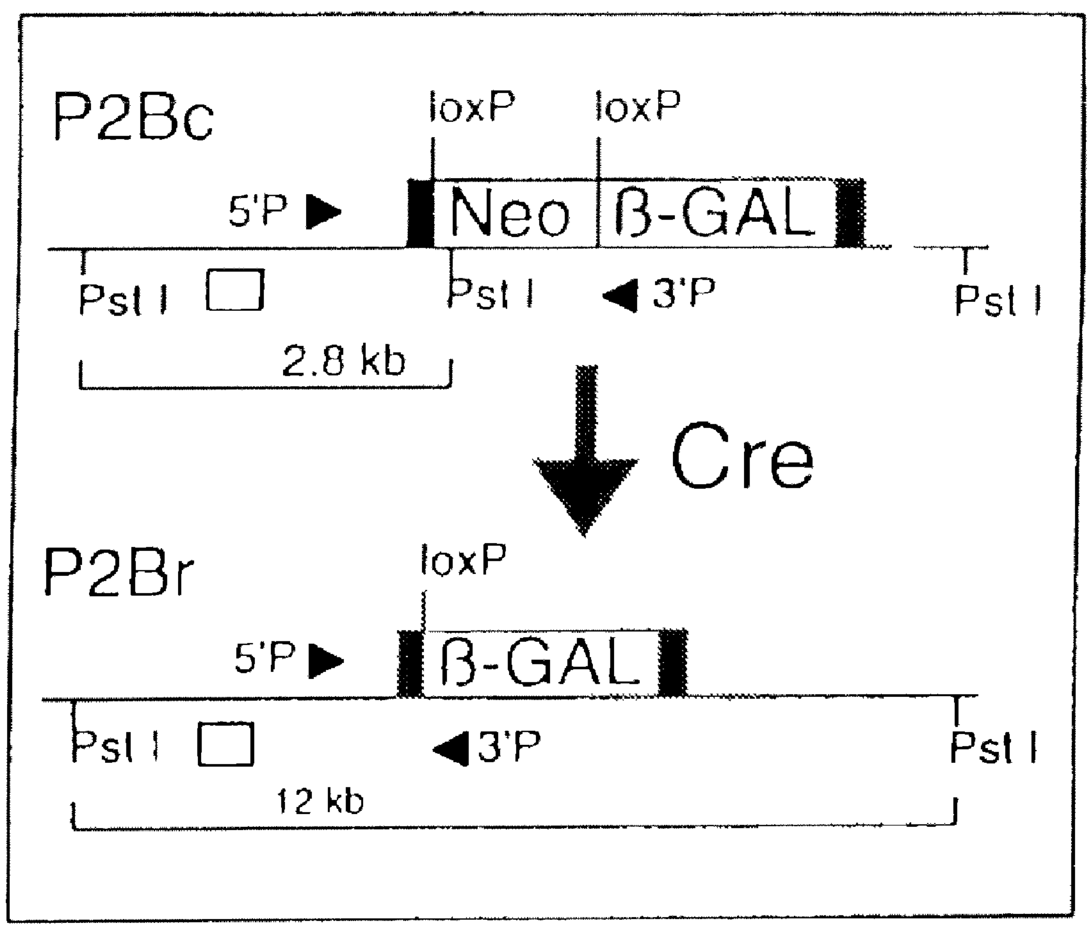
FIG. 1 illustrates a schematic of P2Bc and P2Br alleles. The positions of the PCR primers used (5'P and 3'P) are indicated on the diagrams of the P2Bc and P2Br alleles.

In accordance with the present invention, there are provided nucleic acid constructs comprising a germline-specific promoter operatively associated with a recombinase coding sequence.

As used herein, the term "promoter" refers to a specific nucleotide sequence recognized by RNA polymerase, the enzyme that initiates RNA synthesis. The promoter sequence is the site at which transcription can be specifically initiated under proper conditions. The recombinase nucleic acid(s), operatively linked to the suitable promoter, is (are) introduced into the cells of a suitable host, wherein expression of the recombinase nucleic acid(s) is (are) controlled by the promoter.

Germline-specific promoters contemplated for use in the practice of the present invention include the protamine 1 gene promoter, the protamine 2 gene promoter, the spermatid-specific promoter from the c-kit gene (Albanesi et al. (1996) *Development* 122(4): 1291-1302), the sperm specific promoter from angiotensin-converting enzyme (Howard et al. (1993) *Moll Cell Biol* 13(1):18-27; Zhou et al. (1995) *Dev Genet.* 16(2):201-209), oocyte specific promoter from the ZP2 gene, oocyte specific promoter from the ZP2 gene, oocyte specific promoter from the ZP3 gene (Sehickler et al. (1992) *Moll Cell Biol* 12(1):120-127), and the like.

In addition to the above-described germline-specific promoters, tissue-specific promoters specific to plants are also contemplated for use in the practice of the present invention, including, for example, the LAT52 gene promoter from tomato, the LAT56 gene promoter from tomato, the LAT59 gene promoter from tomato Eyal et al. (1995) *Plant Cell* 7(3):373-384), the pollen-specific promoter of the *Brassica* S locus glycoprotein gene (Dzelzkalns et al. (1993) *Plant Cell* 5(8):855-863), the pollen-specific promoter of the NTP303 gene (Weterings et al. (1995) *Plant J* 8(1):55-63), and the like.

Recombinases contemplated for use in the practice of the present invention include Cre recombinase, FLP recombinase, the R gene product of *Zygosaccharomyces* (Onouchi et al. (1995) *Mol Gen Genet.* 247 (6):653-660), and the like.

Presently preferred constructs contemplated for use in the practice of the present invention include ProCre (comprising the protamine 1 gene promoter operatively associated with Cre recombinase), ProFLP (comprising the protamine 1 gene promoter operatively associated with FLP recombinase). ProR (comprising the protamine 1 gene promoter operatively associated with the R gene product of *Zygosaccharomyces*), and the like.

In accordance with another embodiment of the present invention, there are provided nucleic acid constructs comprising a conditional promoter or a tissue-specific promoter operatively associated with a recombinase coding sequence.

Promoters contemplated for control of expression of recombinase nucleic acid(s) employed in accordance with this aspect of the present invention include inducible (e.g., minimal CMV promoter, minimal TK promoter, modified MMLV LTR), constitutive (e.g., chicken β-actin promoter, MMLV LTR (non-modified), DHFR), and/or tissue specific promoters.

Conditional promoters contemplated for use in the practice of the present invention comprise transcription regulatory regions that function maximally to promote transcription of mRNA under inducing conditions. Examples of suitable inducible promoters include DNA sequences corresponding to: the *E. coli* lac operator responsive to IPTC (see Nakamura et al., *Cell,* 18:1109-1117, 1979), the metallothionein promoter metal-regulatory-elements responsive to heavy-metal (e.g., zinc) induction (see Evans et al., U.S. Pat. No. 4,870, 009), the phage T7lac promoter responsive to IPTG (see Studier et al., *Meth Enzymol.,* 185:60-89, 1990; and U.S. Pat. No. 4,952,496), the heat-shock promoter; the TK minimal promoter; the CMV minimal promoter; a synthetic promoter; and the like.

Exemplary constitutive promoters contemplated for use in the practice of the present invention include the CMV promoter, the SV40 promoter, the DHFR promoter, the mouse mammary tumor virus (MMLV) steroid-inducible promoter, Moloney murine leukemia virus (MMLV) promoter, elongation factor 1α (EFIα) promoter, albumin promoter, APO A1 promoter, cyclic AMP dependent kinase II (CaMKII) promoter, keratin promoter, CD3 promoter, immunoglobulin light or heavy chain promoters, neurofilament promoter, neuron specific enolase promoter, L7 promoter, CD2 promoter, myosin light chain kinase promoter, HOX gene promoter, thymidine kinase (TK) promoter, RNA Pol II promoter, MYOD promoter, MYF5 promoter, phophoglycerokinase (PGK) promoter, Stfl promoter, Low Density Lipoprotein (LDL) promoter, chicken β-actin promoter (used in conjunction with ecdysone response element) and the like.

As readily understood by those of skill in the art, the term "tissue specific" refers to the substantially exclusive initiation of transcription in the tissue from which a particular promoter, which drives expression of a given gene, is derived (e.g., expressed only in T-cells, endothielial cells, smooth muscle cells, and the like). Exemplary tissue specific promoters contemplated for use in the practice of the present invention include the GH promoter, the NSE promoter, the GFAP promoter, neurotransmitter promoters (e.g., tyrosine hydroxylase, TH, choline acetyltransferase, ChAT, and the like), promoters for neurotropic factors (e.g., a nerve growth factor promoter, NT-3, BDNF promoters, and the like), and so on.

In accordance with yet another embodiment of the present invention, there are provided embryonic stem cells containing a nucleic acid construct as described herein.

As readily understood by those of skill in the art, the above-described constructs can be introduced into a variety of animal species. such as, for example, mouse, rat, rabbits, swine, ruminants (sheep, goats and cattle), humans, poultry, fish, and the like. Transgenic amphibians, insects, nematodes, and the like, are also contemplated. Members of the plant kingdom, such as, for example, transgenic mono- and dicotyledonous species, including important crop plants, i.e., wheat, rice, maize, soybean, potato, cotton, alfalfa and the like, are also contemplated.

For example, pluripotential ES cells can be derived from early preimplantation embryos, preferably the ova are harvested between the eight-cell and blastocyst stages. ES cells are maintained in culture long enough to permit integration of the promoter-recombinase nucleic acid construct(s). The cells are then either injected into a host blastocyst, i.e, the blastocoel of the host blastocyst, or cocultured with eight-cell to morula-stage ova, i.e, zona-free morula, so that transfected ES cells are preferentially incorporated into the inner cell mass of the developing embryo. With blastocyst injection, transgenic offspring are termed "chimeric," as some of their cells are derived from the host blastocyst and some tracisfected ES cells. The host embryos are transferred into intermediate hosts or surrogate females for continuous development.

The transformation procedure for plants usually relies on the transfer of a transgene carrying a particular promoter construct via the soil bacterium *Agrobacterium tumefaciens*. Transformation vectors for this procedure are derived from the T-DNA of *A. tumefaciens*, and transgenes are stably incorporated into the nuclear genome. The activity of the transgenes can then be monitored in the regenerated plants under different conditions. In this way, many promoter elements that are involved in complex regulatory pathways such as light responsiveness or tissue specificity have been defined.

Alternatively, direct (i.e., vectorless) gene transfer systems are also contemplated including chemical methods, electroporation, microinjection, biolistics, and the like. Protoplasts isolated from the plants can be obtained by treatment with cell wall degrading enzymes-DNA can be introduced into plant protoplasts by a number of physical techniques including electroporation and polyethylene glycol treatment in the presence of MgCl. The method of choice for rapid promoter analyses in plants is the biolistic method. This technique involves the delivery of the particular DNA construct into plant cells by microprojectiles, i.e., nucleic acid(s) coated or precipitated by tungsten or gold. This method is not limited to any particular plant species or tissue type. Preferably, this method would allow quantitative analysis of transformation if appropriate selectable markers are included.

In a preferred embodiment, the genome of embryonic stern cells according to the invention comprise a transcriptionally active selectable marker flanked by two recombination target sites. It is especially preferred that the recombinase encoded by the recombinase coding sequence operatively associated with a germline-specific promoter is selective for the recombination target sites flanking said selectable marker.

Optionally, embryonic stem cells according to the invention may further comprise one or more of:

a nucleic acid fragment flanked by two recombination target sites, wherein said recombination target sites are different than the recombination target sites which flank said selectable marker.

a nucleic acid construct comprising a conditional promoter operatively associated with a recombinase coding sequence.

a second nucleic acid construct comprising a tissue-specific promoter operatively associated with a second recombinase coding sequence, or the like. Preferably, the second recombinase coding sequence will be different than the first recombinase coding sequence.

The ability to select and maintain nucleic acid constructs in the host cell is an important aspect of an expression system. The most important type of selectable marker incorporated in the nucleic acid construct is an antibiotic resistance element allowing selection with ampicillin, kanamycin, neomycin, tetracycline, hygromycin, puroncycin, blastophycin, and the like. Other approaches employ specially constructed host cells which require the selectable marker for survival. Such selectable markers include the valine tRNA synthetase, vat S, the single-stranded DNA binding protein, ssb, thymidine kinase, or the like. Alternatively, naturally occurring partition systems that maintain copy number and select against plasmid loss is also contemplated. An example is the incorporation of the parB locus. Other selectable markers include HPRT and the like.

Selectable markers specific for plants include, the gus A (iud A), the bar gene, phosphinothricin and the like.

In accordance with still another embodiment of the present invention, there are provided methods for excision of the transcriptionally active selectable marker from the above-described embryonic stem cells, said method comprising:

passaging the genome derived from said embryonic stem cells through gametogenesis (i.e., spermatogenesis or oogenesis).

Excision of marker as contemplated herein can cause a variety of end results, e.g., deletion of the marker or a nucleic acid sequence, gain of function or loss of function, replacement of function, and the like, as well as modulation of any one or more of these results.

Functions which are contemplated to be manipulated include regulating body size and growth rate, including recombining gene constructs which contain various growth hormone gene sequences. Other productivity traits that are targets include altering the properties or proportions of caseins, lactose, or butterfat in milk, increased resistance to viral and bacterial diseases (i.e., "constitutive immunity" or germ-line transmission of specific, recombined antibody genes), more efficient wool production, and the like. Other functions which are contemplated to be modulated include development of lines of transgenic animals and plants for use in directing expression of transgenes encoding biologically active human proteins.

Agronomic traits which are contemplated to be modulated by use of the present invention include tolerance to biotic and antibiotic stresses, increased resistance to herbicides, pest damage, and viral, bacterial, and fungal diseases, improvement of crop quality (i.e., increase in nutritional value of food and feed), reduction of post-harvest losses, improvement of suitability acid enlargement of the spectrum for processing (i.e., altered quantity and composition of endogenous properties, production of new compounds of plant or non-plant origin such as biopolymers or pharmaceutical substances).

In accordance with a still further embodiment of the present invention, there are provided methods for the production of recombinant alleles, said method comprising:

introducing a nucleic acid fragment flanked by at least two recombination target sites into embryonic stem cells as described herein, and passaging the genome derived from said embryonic stem cells through gametogenesis.

As readily recognized by those of skill in the art, nucleic acid fragments can be introduced into ES cells by a variety of techniques, e.g., by homologous recombination, random insertion, retroviral insertion, site specific-mediated recombination, and the like.

Nucleic acid fragments contemplated for use herein include fragments containing an essential portion of a gene of interest.

In accordance with yet another embodiment of the present invention, there are provided methods for the production of recombinant alleles, said method comprising:

introducing at least one recombinase responsive construct into embryonic stem cells as described herein, wherein said construct(s) comprise(s) a nucleic acid fragment and a selectable marker.

wherein said selectable marker is flanked by a first pair of recombination target sites, and wherein said nucleic acid fragment is flanked by a second pair of recombination target sites, passaging the genomic derived from said embryonic stem cells through gametogenesis.

In a presently preferred aspect, this first pair of recombination target sites is recognized by a recombinase which is expressed under the control of a germline-specific promoter and said second pair of recombination target sites is recognized by a recombinase which is expressed under the control of a conditional promoter or a tissue specific promoter.

Optionally, the embryonic stem cells employed herein can further comprise a second nucleic acid construct selected from constructs comprising a conditional promoter operatively associated with a recombinase coding sequence, a construct comprising a tissue-specific promoter operatively associated with a recombinase coding sequence, acid the like.

In accordance with still another embodiment of the present invention, there are provided methods for the conditional assembly of functional gene(s) for expression in eukaryotic cells by recombination of individual inactive gene segments from one or more gene(s) of interest, wherein each of said segments contains at least one recombination target site, and wherein at least once of said segments contains at least two recombination target sites, said method comprising:

introducing said individual inactive gene segments into an embryonic stem cell as described herein, thereby providing a DNA which encodes a functional gene of interest, the expression product of which is biologically active, upon passage of the genomic derived from said stem cells through gametogenesis.

For assembly of functional genes from inactive gene segments, see, for example, U.S. Pat. No. 5,654,182, incorporated herein by reference in its entirety.

In accordance with a still further embodiment of the present invention, there are provided methods for the generation of recombinant livestock, said method comprising:

combining embryonic stem cells that include nucleic acid construct according to the invention with host pluripotential ES cells derived from early preimplantation embryos, and introducing these combined embryos into a host female and allowing the derived embryos to come to term.

In accordance with yet another embodiment of the present invention, there are provided methods for the generation of recombinant plants, said method comprising transforming plant zygotes with nucleic acid constructs according to the invention and allowing the zygote to develop.

The objective of the current work with ProCre nucleic acid constructs was to determine the potential of germline-specific promoters to implement efficient approaches utilizing site-specific recombinases to generate an array of sophisticated mutations in mammals and plants. The data shows that it is possible to create recombinase nucleic acid constructs that are expressed at high levels in the germ line but not to a functionally significant extent in either ES cells or embryonic or adult somatic tissues. Homologous recombinants with a selectable marker can be isolated in ES cells that contain promoter-recombinase nucleic acid constructs. Transgenic animals and plants bearing the promoter-recombinase nucleic acid constructs and a target allele transmit the recombined target to their progeny at high frequencies. These results establish the principle that mammals and plants containing loci that have been homologously recombined and then subsequently site-specifically recombined can be generated simply by using ES cells with a suitable recombinase nucleic acid constructs for the initial targeting. By this mechanism, alleles containing a single recombinase target site and a mutation of interest can be produced in the progeny of ES cell chimeras without any investment of time, expertise, or resources over that required to create an allele that still contains a selectable marker. The paradigm has obvious utility in the production of subtle and conditional mutations that require generation of alleles with minimal structural alterations. Because the presence and transcriptional activity of selectable markers can contribute to phenotypes in an unanticipated and unwanted manner (Fiering et al. (1995) *Genes Dev* 9:2203-2213); Olson et al (1996) *Cell* 85:14), the approach will also be useful for generating null alleles.

Expression of the endogenous mP1 locus (Hecht et al. (1986) *Exp Cell Res* 164:183-190), and mP1-driven nucleic acid constructs (Behringer et al. (1988) *Proc Natl Acad Sci USA* 85:2648-2652; Braun et al. (1989) *Nature* 337:373-376; Zambrowicz et al. (1993) *Proc Natl Acad Sci USA* 90:5071-5075) is restricted to haploid spermatids. Expression of mP1 nucleic acid construct expression typically begins at haploid stages, and both RNA (Caldwell and Handel (1991) *Proc Natl Acad Sci USA* 88:2407-2411) and proteins (Braun et al. (1989) *Nature* 337:373-376) diffuse through the spermatogenic syncytium. The result is a highly efficient recombination of target alleles and the segregation of recombinase and target nucleic acid constructs in the first generation.

Cre-mediated recombination proved to be highly testis-specific in ProCre mice. It is clear that the nucleic acid constructs are not expressed in the inner cell mass or in other early embryonic tissues. Cells from pre-implantation embryos intermingle extensively and the embryo as a whole is derived from a small number of cells (Beddington et al. (1989) *Development* 106: 37-46; Soriano and Jaenisch (1986) *Cell* 46:19-29). If ProCre nucleic acid constructs recombined target sequences during preimplantation stages, at least a few percent of the cells in many tissues would contain the P2Br allele and Southern and PCR analyses showed that this was not the case. The ectopic Cre activity seen in some ProCrc strains probably resulted from low levels of recombinase expression in later embryos or mature tissues, a finding consistent with the expression patterns of other mP1-driven nucleic acid constructs. Northern analyses have failed to reveal the expression of mP1-containing nucleic acid constructs in a variety of mature tissues (Peschon et al. (1987) *Proc Natl Acad Sci USA* 84:5316-5319; Behringer et al. (1988) *Proc Natl Acad Sci USA* 85:2648-2652; Peschon et al. (1989) *Ann N Y Acad Sci* 564:186-197; Zambrowicz et al. (1993) *Proc Natl Acad Sci USA* 90:5071-5075), but nucleic acid constructs containing the mP1 promoter and the SV40 T-antigen led to the consistent development of tumors of the petrosal bone and right cardiac atrium (Behringer et al. (1988) *Proc Natl Aced Sci USA* 85:2648-2652).

PCR assays represent a very sensitive assay for whether sufficient levels of Cre protein were produced to effect recombination. Importantly, they measured the cumulative level of recombination, for events that occurred at any stage of development are likely to have been propagated to, and might be amplified in, descendant populations. The highest level of ectopic recombination was that observed in cardiac ventricular tissue of strain which generated a signal approximately equivalent to that expected if the ratio between recombined and unrecombined alleles were 1:104. The activities observed in other strains were considerably lower than this, and one strain did not show any ectopic activity. None of the strains showed evidence of recombination in the cardiac atria and the petrosal bone was not examined. These assays did not rule out the possibility that higher levels of recombination occur in tissues that were not examined or that the low levels of recombination observed in some tissues reflected high levels of recombination in some component cell population.

These low levels of ectopic activity suggest that mP1-driven recombinase nucleic acid constructs could be used for the production of embryos containing genetically lethal alleles. Some alleles created by homologous recombination in ES cells will prove to be lethal in heterozygotes, as was the case for mRNA editing mutation of the GluR2 glutamate receptor subunit (Brusa et al. (1995) *Science* 270:1677-160). Germline transmission would be restricted to rare chimeras in which time level of chimerism was low enough in tissues affected by the mutation to allow survival and high enough in the germline to allow transmission. This problem could be circumvented by creating recombinase-conditional mutations in ES cells bearing mpl-recombinase nucleic acid constructs, or by making the same mutations in standard ES cells and then introducing the mpl-recombinase nucleic acid construct by breeding. So long as the recombined version of the allele did not adversely impact terminal stages of spermatogenesis, embryos containing the recombined allele could be efficiently produced. Embryos containing recombined nucleic acid constructs can also be produced through the activity of Cre nucleic acid constructs that are expressed during early embryogenesis from the human cytomegalovirus minimal promoter (Schwenk et al. (1995) *Nucleic Acids Res* 23:5080-5081), the adenovirus Ella promoter (Lakso et al. (1992) *Proc Natl Acad Sci LSA* 89:6232-6236), or the zP3 promoter (Lewandoski et al. (1997) *Curr Biol* 7:148-151) ProCre and zP3 nucleic acid constructs have the advantage of delivering a recombined allele to the zygote, guaranteeing that all cells in the derived embryos will contain the allele.

ProCre cells are but one of many different kinds of recombinase-bearing ES cells that could significantly shorten the time and effort required for a wide variety of genetic manipulations in mice. The most obvious of these are complimentary ProFLP ES cells in which the FLP recombinase was derived from *S. cerevisae* (Broach and Hicks (1980) *Cell* 21:501-508) or another species (Kuhn et al. (1995) *Science* 269:1427-1429). Conceptually distinct from these but perhaps as generically useful would be ES cells bearing inducible recombinase nucleic acid constructs that would facilitate temporal control of recombinase expression in ES cells, chimeras, and heir progeny to generate site-specifically recombined alleles (Araki et al (1992) *J Mol Biol* 225:25-37: No et al. (1996) *Proc Natl Acad Sci USA* 93:3346-3351, Logie and Stewart (1995) *Proc Natl Acad Sci USA* 92:5940-5944; Feil et al. (1996) *Proc Natl Acad Sci USA* 93:10887-10890). Finally, fusion genes that led to recombinase expression in specific tissues could be used to address specific research objectives.

The invention will now be described in greater detail by reference to the following non-limiting examples.

Example 1

Mammalian DNA Constructs

A 652 bp fragment of the mP1 promoter (SEQ ID NO:1; Peschon et al. (1989) *Annals of the New York Academy of Sciences* 186-197) was isolated by PCR using PCR primers (SEQ ID NOs:2 and 3) genomic DNA from CCE ES cells (Robertson et al. (1986) *Nature* 323:445-448) as a template. This fragment was fused to a Cre coding sequence (SEQ ID NO:4) modified to contain a consensus translation start site (Kozak (1986) *Cell* 44:283-292), 11 codons for a human c-myc epitope (Evan et al. (1985) *Mol Cell Biol* 5:3610-3616), 7 codons for a minimal SV40 nuclear localization signal (Kalderon et al. (1984) *Cell* 39:499-509) and the polyadenylation sisal from pIC-Cre in the plasmid pOG304M (SEQ ID NO:5). The Cre expression plasmid pOG231 was prepared by fusing a Cre coding sequence modified from pIC-Cre (Gu et al. (1993) *Cell* 73:1155-1164), and containing the same translation start and nuclear localization signal, to the synthetic intron and CMV promoter of pOG44 (O'Gorman et al. (1991) Science 251:1351-1355).

A plasmid, pOG277 (SEQ ID NO:7), containing a loxP-flanked neomycin cassette was prepared by inserting a wild-type loxP site (SEQ ID NO:8; Hoess et al. (1982) *Proc Natl Acad Sci USA* 79:3398-402) into pBSKS (Stratagene) and then cloning the neomycin expression cassette from pMClneo-polyA (Thomas et al. (1987) *Cell* 51:503-512) between interations of this loxP site. The hoxb-1 targeting construct consisted of the PCGK-TK cassette from pPNT (Tybulewicz et al. (1991) *Cell* 65:1153-63), and 1.4 kb) and 10.2 kb of sequences 5' and 3' to an Nru I site 800 bp 5' to the hoxb-1 transcriptional start site isolated from a 129 strain genomic library (Stratagene). The loxP-flanked neo cassette from pOG277 was inserted into the NruI site. The pOG277 neomycin cassette and a β-GAL sequence was inserted into the first exon of the large subunit of RNA polymerase II (RP2) (Ahearn et al. (1987) *J. Biol. Chem.* 262:10695-10705) to create the P2Bc allele (FIG. 1). Cre-mediated recombination of the P2Bc allele results in the deletion of the neomycin cassette (Neo) of P2Bc that is flanked by two loxP sites, leaving a single loxP sire and fusing the B-Gal coding sequence to the initial codons of the RNA polymerase II coding sequence. Recombination increases the size of a Pst I fragment recognized by the RP2 probe, which is external to the targeting vector used, indicated by the shaded box below each allele.

Example 2

Production of Transgenic Mice

Fertilized oocytes obtained from matings of 129/SvJae (Simpson et al. (1997) *Nat Genet.* 16:19-27) and BALB/c× C57BL/6 F1 mice were used for pronuclear injections of (the Protamine-Cre fusion gene from pOG304M according to standard protocols (Hogan et al. Manipulating the Mouse Embryo: The Manual, Coldspring Harbor Press (1994), pg. 497). Production of ES cells and homologous recombinants: Heterozygous ProCrc 129/Svjac males were mated to 129/SvEms-+–$^{?}$/J females (Simpson et al. (1997) *Nat Genet.* 16:19-27) to produce blastocysts that were cultured according to standard protocols (Robertson (1987) Teratocarcinomas and embryonic stem cells, a practical approach, eds. E. J. Robertson (IRL Press), pp. 71-112). The sex (King et al. (1994) *Genomics* 24:159-68) and ProCre status of each line were determined by PCR assays. Molecular analyses: Tail biopsy genomic DNA was used for hybridization assays or PCR assays to identify ProCre and P2Bc/r mice. PCR reactions for the detection of ectopic Crc activity used 100 ng of genomic DNA as a template to amplify a P2Br-specific product using a 5' primer from the RP2 promoter and a 3' primer from the β-GAL coding sequence (FIG. 1). Thirty cycles of amplification were done in a total volume of 100 μl using 300 ng of each primer, 3 mM MgCl2, 1.5 units of Taq polymerase, and an annealing temperature of 60° C. Southern blots of reaction products were hybridized with a probe specific for the P2Br reaction product.

Example 3

ProCre Nuclei Acid Constructs Efficiently Recombine Target Alleles

A total of nine founder animals with ProCre nucleic acid constructs were obtained from injections of a Protamine-Cre fusion gene. Two lines were derived from injections of 129SvJae (Simpson et. al. (1997) *Nat Genet.* 16:19-27) embryos, and seven from injections of CB6F2 embryos. The 129/SvJae lines and three randomly selected hybrid lines were examined in detail. To determine whether ProCre nucleic acid constructs would efficiently recombine a target allele, males were generated that contained a ProCre nucleic acid construct and a target for Cre-mediated recombination. This "P2Bc" (Pol II, β-Gal, conditional) target (FIG. 1) was created using homologous recombination in ES cells to insert a loxP-flanked neomycin cassette and a β-GAL coding sequence into the first exon of the locus coding for the large subunit of RNA polymerase II. Crc-mediated recombination of the loxP sites was expected to delete the intercalated sequences, creating "P2Br" allele (Pol II, β-Gal, recombined).

These males were mated to wild-type females and the resulting progeny were examined by Southern blotting to determine if they inherited the P2Bc or the P2Br allele, and to additionally determine the segregation pattern of ProCre nucleic acid constructs anti P2Br alleles. Southern blot of Pst I digested tail biopsy DNA's from a +/P2Bc, +/ProCre male (sire) and four of his progeny by a wild-type female probed with n RP2 probe (top) and then reprobed with a Cre probe (bottom). The large majority of transmitted target alleles were Cre-recombined P2Br alleles (Table 1). ProCre nucleic acid constructs and recombined target alleles segregated independently in the first generation approximately 50% of mice that inherited a P2Br allele also inherited their male parent's ProCre nucleic acid construct. All RP2 mutant alleles in the progeny were P2Br, and some progeny inherit a P2Br allele without inheriting ProCre nucleic acid construct and is homozygous wild-type at the RP2 locus. These data establish that ProCre nucleic acid constructs efficiently recombine the P2Bc allele in the male germline and that the recombined P2Br alleles and ProCre nucleic acid constructs segregate in the first generation. Because significantly more than 25% of the progeny inherited recombined target alleles, recombination either occurred during diploid stages of spermatogenesis or Crc generated during haploid stages of spermatogenesis was distributed among spermatids through cytoplasmic bridges (Braun et al. (1989) *Nature* 337:373-376), effecting recombination in spermatids that did not themselves contain a ProCre nucleic acid construct.

The progeny of matings between ProCre males and +/P2Bc females were also examined to determine if male gametes from ProCre mice delivered through Cre to zygotes to effect Cre-mediated recombination of a target sequence. Of 96 progeny examined by Southern blotting, none contained a Cre-recombined P2Br allele.

It has also been discovered that a loxP-flanked neo cassette in the glutamate receptor P6 subunit locus is efficiently recombined by ProCre nucleic acid constructs in mice.

Example 4

ProCre Nucleic acid construct Expression is Highly Tissue-Specific

Genomic DMAs from ten different tissues of five-to seven-week old males that contained both a ProCre nucleic acid construct and a P2Bc target allele were analyzed in Southern blots. Southern blots were prepared of Pst I digested DNA from testes (T) and one other tissue (K, kidney B, brain; S, spleen) of males heterozygous for one of four ProCre nucleic acid constructs and the P2Br allele. Testis DNA from each male shows a P2Br allele signal, in addition to those generated by the wild-type RP2 (WT) and P2Bc alleles. Other tissues show only the WT and P28c signals. Only the testis samples showed signal indicating Cre-mediated recombination of the target. The intensity of the P2Br signal relative to that of the wild-type allele ranged from 0% to 22% for different ProCre strains and did not correlate with the ProCre nucleic acid construct copy number. The copy number of ProCre nucleic acid constructs varied among lines showing similar levels of recombination in testis. For example, restriction patterns and densitometric analyses showed that line 58 contained a single copy of the ProCre nucleic acid construct, yet showed virtually the same testis recombination signal as line containing more than 10 copies. This variability is similar to results obtained with other mP1 promoter-driven nucleic acid constructs (Peschon et al. (1987) *Proc Natl Acad Sci USA* 84:5316-5319; Zambrowicz et al. (1993) *Proc Natl Acad Sci USA* 90:5071 5075).

As a more sensitive measure of ectopic recombination, PCR amplifications were performed on the same samples. The amplification primers were expected to produce a 325 bp product from the recombined target and a 1.4 kb fragment from the unrecombined allele (FIG. 1). The assay was expected to measure the cumulative level of recombination, for any P2Br alleles formed during transient expression of Cre during development would be preserved and perhaps amplified in descendant cells. Low levels of ectopic recombination product were observed in some tissues of all ProCre lines except for one. A Southern blot of PCR amplification products of the P2Br allele utilized tissues from a male heterozygous for the ProCre nucleic acid construct and the P2Bc allele. DNA from 10 different tissues was amplified using primers and conditions that produced a 350 bp product from the recombined, P2Br allele. Each lane contains 10% of the reactions, except for the testis reactions which were diluted 500 (T5), 250 (T2) and 100 (T1) fold prior to loading, and a liver reconstruction control (C), which was diluted 1:100 before loading. The highest level of ectopic activity was observed in cardiac ventricular muscle of mice; in these samples the ectopic signal was more than 100 fold lower than that observed in testis. Three strains showed much lower levels of recombination in brain tissue, and strain 75 additionally showed ectopic activity in spleen. Despite the difficulty of quantifying PCR results, these data clearly indicate that ectopic activity occurred at very low levels in most tissues of most ProCre lines.

Example 5

Isolation of Homologously Recombined ProCre ES Cell Clones Using Targeting Vectors with a LoxP-Flanked Selectable Marker Four male +/ProCre ES cell lines were established from 129/Sv strain ProOre transgenic mice. In preliminary experiments, passage 5 cells from one of these lines (PC3) were used to generate three male chimeras with between 50 and 95% coat color chimerism. In matings with C57BL/6 females, two of these male chimeras have sired a total of 11 pups, all bearing the Agouti coat color signifying germline transmission of the ES cell genome, and 6 of 9 pups genotyped additionally contained the line 70 ProCre nucleic acid construct. The frequency of germline transmission has not yet been determined, nor has it been determined whether competency for germline transmission will persist in homologously recombined ProCre ES cells at later passages.

Figure 2:
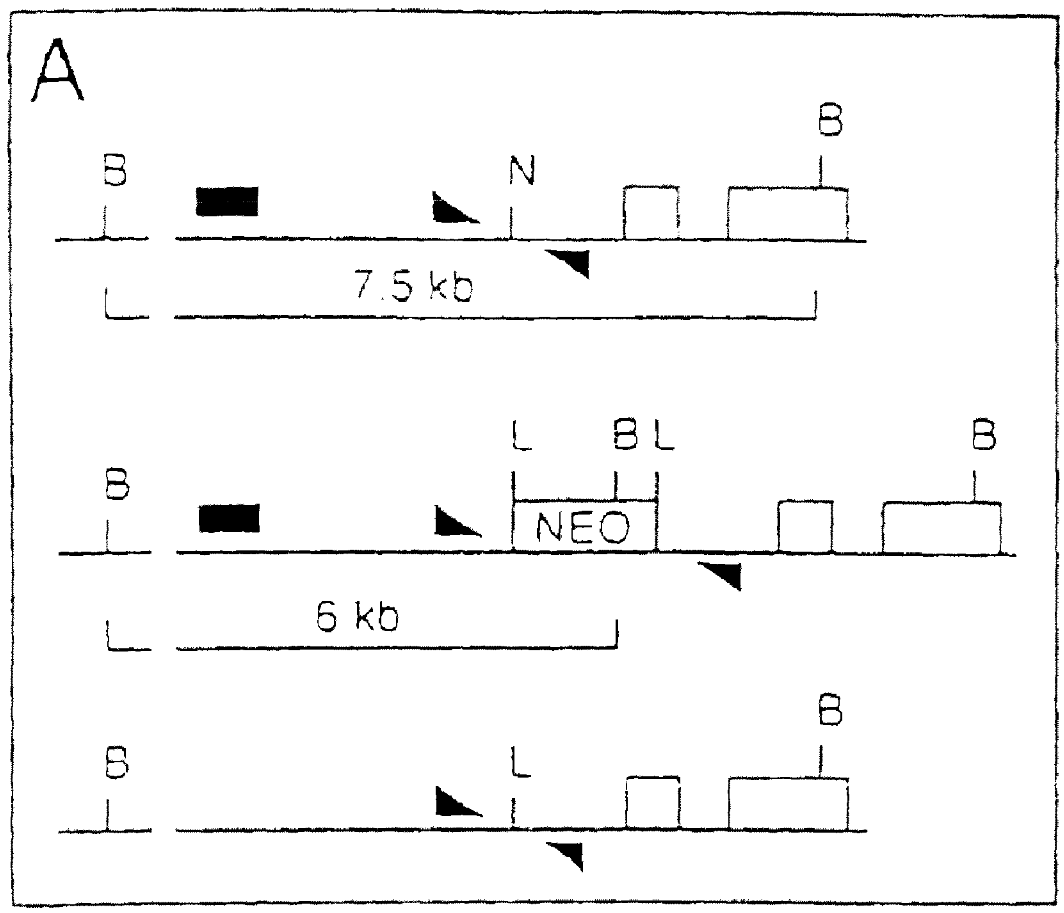
FIG. 2 depicts the targeting of the hoxb-1 locus in ProCre ES cells using a targeting vector that contains a loxP-flanked selectable marker. Top, schematic of the wild-type hoxh-1 locus showing the positions of the two exons (open boxes), the position of a 5' NruI site and flanking BamHI restriction endonuclease sites, and PCR primers (triangles) that amplify a 204 bp product from the wild-type allele that includes the NruI site. Middle, the predicted organization of homologously recombined hoxb-1 allele in which a neomycin cassette (NEO), flanked by loxP sites (L), bias been inserted into the NruI site shown in the top diagram. The insertion creates a novel BamHI site and the same PCR primers now amplify a 1600 bp product. Bottom: the predicted structure of the recombined allele shown in the middle panel after Cre-mediated excision of the neomycin cassette to leave a single loxP site in place of the NruI site of the wild-type allele. Amplification with the same primers now yields a 268 hp product.

To determine if homologously recombined ProCre ES cell clones could be isolated using targeting vectors that contained a loxP-flanked selectable marker, two transfections were done using variants of a targeting, vector in which a loxP-flanked neomycin cassette was inserted into an Nru I site in the hoxb-1 locus promoter (FIG. 2). A Southern blot of BamRi-digested genomic DNAs were harvested from a 96-well plate from 10 doubly-selected ES cell clones and hybridized with a probe (shown in FIG. 2) which is external to the targeting construct. All samples as show the 7.5 kb band from the wild-type allele and four clones additionally show the 6 kb band predicted to result from homologous recombination. In these transfections, 12 of 62 (19%) PC3—and 10 of 56 (18%) PCs-derived clones that were ganciclovir and G418-resistant (Mansour et al. (1988) *Nature* 336:348-352) were found to be homologously recombined. In two parallel transfections of CCE cells (Robertson et al. (1986) *Nature* 323:445-8) with the same vectors, 32 of 93 (34%) and 15 of 132 (11%) clones were homologously recombined. The total numbers of G418-resistant clones recovered from ProCre ES cell transfections were reduced relative to the parallel CCE transfections. This may be attributable to both Cre-mediated excision of the neomycin cassette and to the fact that the transfections were done under electroporation conditions optimized for CCE cells.

Because it was formally possible that the homologously recombined clones contained inactive loxP sites, five homologously recombined PC3 ES cell clones and the parental PC3 cell line using the primers shown in FIG. 2 were either mock transfected or transiently transfected with the pOG231 Cre expression vector. For the transient transfection assay, DNA was harvested 48 hours after transfection and used in PCR assays to assess whether the loxP sites in rice recombinant clones could be recombined by Cre. In all cases a clear recombination signal was observed in the pOG231 transfected sample. The recombinant clones and parental cell lines show the 204 bp amplification product of the wild-type allele, and the recombinant clones additionally show, a 1600 bp product (1600) resulting from amplification across the neomycin cassette and a nonspecific 1100 bp amplification product (NS). The pOG231-transfected recombinant clones show an additional 268 bp product signaling the Cre-mediated excision of the neomycin cassette from the recombinant alleles of some cells. Experiments were also done to assess the stability of the loxP-flanked neo cassette in ProCre ES cells. Five recombinant clones were grown in the presence of G418 for two weeks, and then aliquots of each were grown either in the presence or absence of G418 for a further 10 days. PCR assays were performed to determine if Cre-recombined alleles were present in any of these samples and none was observed in the mock transfected controls. These data suggest that there is not enough Cre activity to significantly influence either the ability to isolate recombinant clones or the stability of the selectable markers in those clones, establishing that the loxP sites in these clones were functional.

To determine if there was any detectable Cre activity in ProCre ES cells, aliquots of two lines (PC3 and PC5) were transiently transfected with the targeting vector used to create the P2Bc allele. DNA was recovered 48 hours after transfection and used for PCR amplifications of the P2Br plasmid molecules that would be generated by extrachromosomal Cre-mediated recombination. Small amounts of recombination product were seen in both ProCre ES cell transfections, and none was observed in parallel samples of CCE ES cells. This shows that the ProCre ES cell lines express sufficient Cre to recombine some extrachromosomal targets when the latter are present at high copy numbers.

Example 6

Plant DNA Constructs

To define sequences in the LAT 52 and LAT59 promoters involved in expression in pollen, proximal promoters were constructed employing a series of linker substitution mutants using the particle bombardment system (Klein et al. (1987) *Nature* 327:70-73; Twell et al. 91989b) *Plant Physiol* 91:1270-1274). These experiments were performed by cobombarding the test plasmids (luciferease [LUC]—recombinase fusions) with reference plasmids (β-glucuronidase [GUS] fusions). The latter served as a control for bombardment variability and allowed comparisons to be made between independent bombardments.

The context of the −100 promoter in LAT52 and the −115 promoter in LAT59 was chosen because these promoters appeared to be the minimal regions that still conferred high levels (25% relative to the available full-length promoter) of pollen-specific expression (Twell et al. (1991) *Gen Dev* 5:496-507). These minimal promoters were then fused to the Cre coding sequence operatively linked to the luc gene (Ow et al. (1986) *Science* 234:856-858) coding region, and the resulting plasmids served as a basis for creating the nucleic acid constructs. The LAT52 linker substitutions were performed in p52LUC, which contain entire LAT52 5' untranslated region (5' UTR). A series of six 9- to 10-bp-long linker substitutions were made in p52LUC, spanning the region-84 to −29 (52LS1 to 52LS6).

Example 7

Tissue Specificity in Plants

The results obtained by transient expression in pollen and in transgenic plants provided information on the effect of the various constructs on expression in pollen but not on their effect on tissue specificity. A tobacco cell culture, TXD (maintained as described by Howard et al. (1992) *Cell* 68:109-118), was, therefore, added as an additional component of the transient assay system. The TXD cell culture was initiated from tobacco mesophyll cells and therefore represents somatic tissue, as opposed to the gametophytic tissue represented by pollen. Cells in culture were chosen, rather than intact tissue, as the somatic tissue source because such cells superficially resemble pollen in that they can be spread out as a monolayer on a plate before bombardment.

In this experiment, translation fusions between the Iuc coding region and either the CaMV 35S promoter drove strong expression in cell culture but negligible expression in pollen, whereas the LAT52 promoter showed the opposite pattern of strong activity in pollen and negligible activity in cell culture. Thus, the transient assay system mimics the expression pattern observed for these promoters in transgenic plants (Twell et al. (1991) *Genes Dev* 5:496-507). This differential expression provided us with a tool with which to address tissue specificity.

Example 8

Plant Transformation and Analysis of Transgenic Plants

Constructs cloned into pBin19 were introduced into tomato (*Lycopersicon esculentum* cv VF36) by *Agrobacterium tumnefaciens* LBA4404 as previously described (McCormick (1991b) Transformation of tomato with *Agrobacterium tumefaciens*, In Plant Tissue Culture Manual, K. Linsey, Ed B6: 1-9). At least 20 independent transformants were obtained for each construct.

For β-glucuronidase (GUS) assays, 5 to 20 μL of pollen, pooled from several flowers of the same plant, was ground directly in Eppendorf tubes in 50 to 100 μL of GUS extraction buffer (Jefferson et al. (1987) *EMBO* 6:3901-3901) using a Teflon-tipped homogenizer driven by a drill. Expression in pollen was measured by fluorometrically assaying GUS activity in supernatrants of pollen extracts using 2 mM 4-methylumbelliferyl β-D-glucuronide (Sigma) as substrate (Jefferson et al. (1987) *EMBO* 6:3901-3907). GUS activity was corrected for variation in total protein content using a bicinchoninic acid protein assay kit (Pierce, Rockford, Ill.).

Expression in leaves, flowers, stems, roots, and seed was tested histochemically by staining with 5-bromo-4-chloro-3-indolyl β-D-glucuronide (Molecular Probes, Eugene, Oreg.) as described previously (Jefferson et al. 91987) *EMBO* 6:3901-3907). Expression in leaves was also analyzed florometrically as given previously.

Example 9

Transient Transformation of tobacco Pollen and Cell Culture

Pollen spread out as a monolayer was bombarded essentially as previously described (Twell et al. (1991) Genes Dev 5:496-507), except that gold was substituted for tungsten and only 1 μg of test plasmid and used per plate. TXD cell culture (maintained as described by Howard et al. (1992) *Cell* 68:109-118) was spread out similarly as a monolayer (1 mL of a 50-mL stationary culture per plate) and bombarded as previously described. Between six and 12 independent bombardments were performed for each construct. In each experiment, the test plasmid was cobombarded with a reference plasmid: pB1223 (Clontech, Palo Alto, Calif.) was used for assays of all constructs in tobacco cell culture; PLAT59-12 (Twell et al. (1990) *Development* 109:705-713) for assays of LAT52 and LAT56 constructs in tobacco pollen; PLAT56-12 (Twell et al. (1990) *Development* 109:705-713) for assays of LAT59 constructs in tobacco pollen. Processing of the tissue after 15 to 16 hr and analysis of GUS and LUC activity were as described previously (Twell et al. (1991) *Genes Dev* 5:496-507). Transient expression was reported as "relative LUC activity," which represents the ratio between the test (LUC) and the reference (GUS) plasmids.

While the invention has been described in detail with reference to certain preferred embodiments thereof, it will be understood that modifications and variations are within the spirit and scope of that which is described and claimed.

The invention claimed is:

1. A nucleic acid construct comprising:

a germline-specific promoter operatively associated with a recombinase coding sequence, and a transcriptionally active selectable marker flanked by two recombination target sites, wherein said germline-specific promoter is the LAT52 gene promoter from tomato, the LAT56 gene promoter from tomato, the LAT59 gene promoter from tomato, the pollen-specific promoter of the *Brassica* S locus glycoprotein gene, or the pollen-specific promoter of the NTP303 gene, and wherein said recombinase coding sequence encodes a recombinase selected from the group consisting of Cre recombinase, FLP recombinase, and the R gene product of *Zygosaccharomyces*.

2. The nucleic acid construct according to claim 1 wherein said germline-specific promoter is the LAT52 gene promoter from tomato.

3. The nucleic acid construct according to claim 1 wherein said germline-specific promoter is the LAT56 gene promoter from tomato.

4. The nucleic acid construct according to claim 1 wherein said germline-specific promoter is the LAT59 gene promoter from tomato.

5. The nucleic acid construct according to claim 1 wherein said germline-specific promoter is the pollen-specific promoter of the *Brassica* S locus glycoprotein gene.

6. The nucleic acid construct according to claim 1 wherein said germline-specific promoter is the pollen-specific promoter of the NTP303 gene.

7. The nucleic acid construct according to claim 1 wherein said recombinase selected is Cre recombinase.

8. The nucleic acid construct according to claim 1 wherein said recombinase selected is FLP recombinase.

9. The nucleic acid construct according to claim 1 wherein said recombinase selected is the R gene product of *Zygosaccharomyces*.

* * * * *